United States Patent [19]

Grummons

[11] Patent Number: 4,988,291
[45] Date of Patent: Jan. 29, 1991

[54] ORTHODONTIC APPLIANCE AND METHOD

[75] Inventor: Duane C. Grummons, Playa DelRay, Calif.

[73] Assignee: Great Lakes Orthodontics, Ltd., Tonawanda, N.Y.

[21] Appl. No.: 276,878

[22] Filed: Nov. 28, 1988

[51] Int. Cl.⁵ ............................................. A61C 3/00
[52] U.S. Cl. .................................................... 433/5
[58] Field of Search ......................................... 433/5

[56] References Cited

U.S. PATENT DOCUMENTS

| | | | |
|---|---|---|---|
| 2,334,894 | 11/1943 | Atkinson | 433/5 |
| 3,814,087 | 6/1974 | Heikes | 433/5 |
| 4,553,933 | 11/1985 | Armstrong | 433/5 |

FOREIGN PATENT DOCUMENTS 2803560  8/1979  Fed. Rep. of Germany .......... 433/5

OTHER PUBLICATIONS

Great Lakes Orthodontic Laboratories, Inc. brochure, May 1979.
Great Lakes Orthodontic Laboratories, Inc. brochure, May 1984.

Primary Examiner—Cary E. Stone
Attorney, Agent, or Firm—Edwin T. Bean, Jr.; Martin G. Linihan; John C. Thompson

[57] ABSTRACT

An orthdontic/facial orthopedic appliance for use in applying a pulling force to select teeth, the associated arch, and or jaw component(s) for moving/modifying and positioning the same. The appliance includes a frame supported primarily on the forward cranial portions of the patient's head and shaped to outline the area of the patient's face lateral to the forehead, eyes, nose and mouth, doe not apply force to the temporo-mandibular joint and is stationary against the face during lower jaw movement. The pulling force is in the form of elastic elements connected at one end to a member fixed to the frame and extending therefrom in a manner to be forward of the patient's mouth when the appliance is in a position of use, and at the other end thereof to selected teeth of the patient such that the pulling force pulls the selected teeth, associated arch, and/or upper jaw component(s) in a direction toward the frame. A strap portion adapted to connect to the frame and to be worn around the head is provided to enhance support and stability of the appliance to the head.

A method of straightening teeth and the associated arch using the orthodontic/facial orthopedic appliance is also described herein.

27 Claims, 1 Drawing Sheet

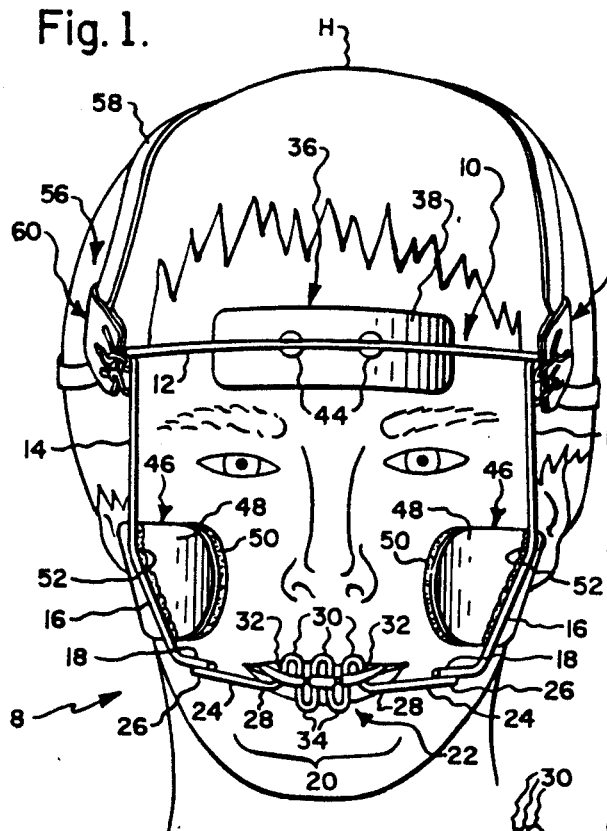
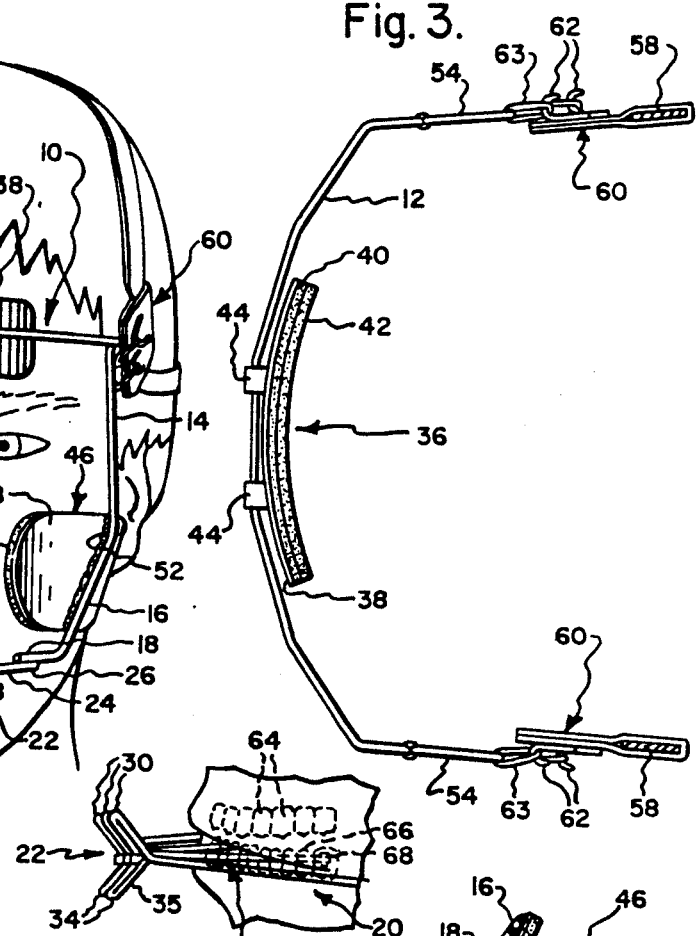
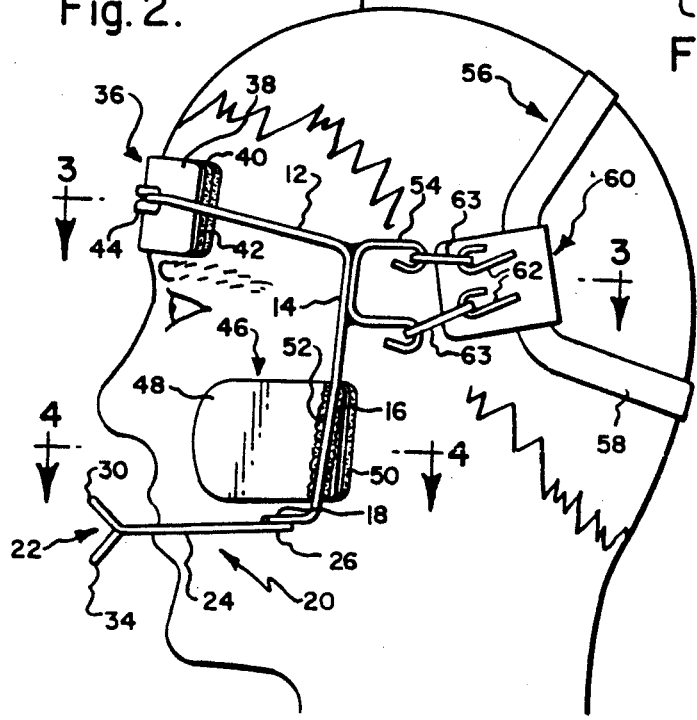
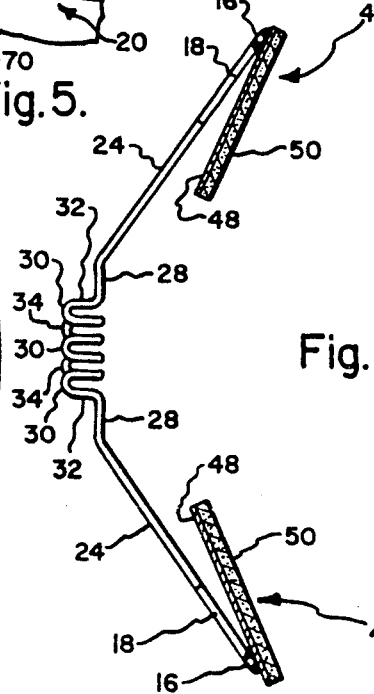

ORTHODONTIC APPLIANCE AND METHOD

FIELD OF THE INVENTION

This invention relates to the field of orthodontic/facial orthopedic appliances, and more particularly to a new and improved face crib for use in applying a pulling force to selected teeth, the associated arch, and/or jaw component(s) for moving and positioning the same

BACKGROUND OF THE INVENTION

Orthodontic anterior traction appliances have been developed which are worn on the head or face of the patient for applying force to selected teeth and/or jaw component(s) to move/modify and position the same. In designing such appliances, important factors to consider are patient comfort including allowing the patient to see clearly and talk while the appliance is worn, adjustability to fit all patients properly, stability of the appliance on the patient's head, and a high degree of versatility in application of force to the patient's teeth and supporting structures.

Typical anterior traction appliances such as a face crib include a frame adapted to be worn on the head of the patient, a forehead rest carried by the frame and adapted to contact the patient's forehead, a chin rest carried by the frame and adapted to contact the patient's chin, and a mouth bow extending forwardly of the patient's mouth when the appliance is in a position of use adapted to be operatively connected by elastic (rubber) bands to selected teeth of the patient. The forehead pad and chin pad function in a manner supporting and positioning the appliance against the patient's face and preventing slippage or undesired movement of the appliance thereby enhancing stability in a manner which is comfortable to the patient.

However, the chin cup is anchored against the patient's chin when providing support and adjustment for the frame. Consequently, lower jaw movement such as that which occurs when talking can cause the movement of the appliance. This, in turn, could interfere with the teeth adjusting process and thereby have a detrimental effect. Further, when the chin cup is in a position of use against the patient's face pressure is exerted against the lower jaw, transmitted unfavorably against the mandibular joint as it relates to the temporal bone and associated disc (meniscus) between (TMJ) which is shown to have a detrimental effect. Therefore, a face crib which is stationary against the patient's face during lower jaw movement and anchored in such a manner that pressure in not exerted against the lower jaw would be desirable.

SUMMARY AND OBJECTS OF THE INVENTION

Accordingly, it is a primary object of the present invention to provide an orthodontic/facial orthopedic appliance for applying force to a patient's teeth and associated arch in a manner whereby the appliance is stationary against the patient's face during lower jaw movement and does not apply force to the temporomandibular joint (TMJ structures). It is a more particular object of the present invention to provide such an appliance which is supported primarily on the forward cranial portions of the patient's head.

It is a further object of the present invention to provide such an appliance which is supported on the patient's face in a relatively stationary position, while also being stabilized by a head strap around the back of the head.

It is a further object of the present invention to provide such an appliance which is comfortable for the patient to wear and does not interfere with vision, speech, swallowing, nor respiratory function.

It is a further object of the present invention to provide such an appliance which is readily adjustable to fit various size patients comfortably and properly.

It is a further object of the present invention to provide such an appliance which affords a high degree of versatility and selectively in supplying force to the patient's teeth and associated arch.

It is a further object of the present invention to provide such an appliance which is relatively simple and efficient in construction, light weight and economical to manufacture.

It is a further object of this invention to provide a new and improved method of straightening teeth, and promoting jaw orthopedic alignment using a combination orthodontic/orthopedic appliance.

In accordance with the invention, an orthodontic/orthodontic appliance is adapted to be worn on the head or face of the patient for providing a pulling force to selected teeth, the associated arch, and/or jaw component(s) for moving/modifying and positioning the same. The orthodontic/orthopedic appliance comprises a frame adapted to be worn on the head of the patient and shaped to outline the area of the patient's face lateral to the forehead, eyes, nose and mouth. A tension-applying means in the form of elastic elements is connected at one end to a member fixed to the frame and extending therefrom in a manner to be forward of the patient's mouth when the appliance is in a position of use, and at the other end thereof to selected teeth of the patient such that the tension mans pulls the selected teeth and/or upper jaw in a direction toward the frame. The frame further includes means adapted to contact the forward cranial region of the patient's head and associated with the tension applying means to reciprocally and simultaneously push against the cranial region when the tension means pulls the teeth, thereby supporting the frame in a relatively stationary position against the patient's head. In particular, there is provided a forehead rest element adapted to contact the forehead region of the patient's head and two spaced cheekbone pad elements adapted to contact the cheekbone region of patient's head. The forehead rest element and cheekbone pad elements are shaped to conform to the patient's forehead and cheekbone, respectively, and are provided with air breathing, anti-friction material for contacting the patient's skin. During use, the tension applying means pulls selected teeth and/or upper jaw forwardly toward the frame while the forehead rest and cheekbone pad elements simultaneously push against the respective cranial portions of the patient's head thereby supporting the frame in a relatively stationary position against the head. A strap portion adapted to connect to the frame and to be worn around the head is provided to enhance support and stability of the appliance to the head.

A method of straightening teeth and the associated arch using the orthodontic appliance of the present invention is described herein. Furthermore, midfacial and upper jaw orthopedic applications also exist.

The above will become more apparent to those skilled in the art after a consideration of the following detailed description taken in conjunction with the accompanying drawings in which a presently preferred form of this invention is illustrated.

BRIEF DESCRIPTION OF THE DRAWINGS

FIG. 1 is a front elevational view of an orthodontic appliance in accordance with the present invention as it would appear in use worn of the head of the patient;

FIG. 2 is a side elevational view of the orthodontic appliance in accordance with the present invention as it would appear in use of the head of the patient;

FIG. 3 is a top plan view looking in the direction from the patient's forehead to the patient's chin of the orthodontic appliance in accordance with the present invention;

FIG. 4 is a bottom plan view looking from the patient's chin upward toward the patient's forehead of an orthodontic appliance in accordance with the present invention; and FIG. 5 is a fragmentary side elevational view illustrating one mode of applying force to a patient's teeth using the orthodontic appliance according to the present invention.

DETAILED DESCRIPTION OF THE ILLUSTRATIVE EMBODIMENT

The orthodontic/facial orthopedic appliance of the present invention is a face crib which comprises a continuous peripheral frame, a forehead element, two spaced cheekbone pad elements and a member fixed to the frame and extending therefrom in a manner to be forward of the patient's mouth when the appliance is in a position of use, and tension force applying means adapted to be connected at one end to the portion and at the other end to a selected tooth such that the tension applying means pulls the selected teeth in a direction toward the frame. As the tension means exerts a force toward the frame the cheekbone and forehead elements simultaneously exert a force on the cranial portion of the patient's face thereby holding the appliance in place on the patient's head. The improvement of the present invention over the prior art comprises support to the face crib entirely against the cranial portions of the patient's head. This is believed to eliminate the possible detrimental effect resulting from movement of the appliance and application of force during lower jaw movement force extended to the temporo mandibular joints due to anchoring the appliance against the lower chin when using a conventional chin cup.

Referring now to the drawings, the face crib, generally indicated 8 shown in a position of use on a patient's head H and in accordance with the present invention comprises a continuous peripheral frame, generally designated 10, preferably of metal such as stainless steel. The frame 10 includes a top portion 12 closely adjacent and conforming to the shape of the patient's forehead, a pair of spaced apart, substantially parallel, upper side portions 14 extending from opposite ends of the top portion 12 and located closely adjacent to the opposite sides of the patient's face including the eye and upper cheekbone regions, a pair of spaced apart lower side portions 16 extending slightly inwardly from opposite ends of the upper side portions 14 and conforming to the opposite sides of the patient's face including the cheekbone regions, a pair of bottom portions 18 extending inwardly from the lower side portions 16 toward the patient's mouth, and a mouth bow, generally indicated 20, connected at opposite ends to the bottom portions 18.

The mouth bow 20 further includes a member generally indicated 22 and disposed forwardly of the mouth of the patient when the face crib is in a position of use. In particular, the mouth bow 20 preferably is of metal and conforms to a wire or rod like form having a diameter less than the diameter of the frame 10. The mouth bow 20 includes a pair of end portions 24 each being connected at one end to a corresponding bottom portion 18 of frame 10 and extending at an angle with respect to a plane passing through the lower side portions 16 and inwardly therefrom. The ends 24 of mouth bow 20 are welded or soldered to the bottom portion 18 of frame 10 a shown at 26. As best illustrated in FIG. 4, the portion 22 of mouth bow 20 further includes a pair of inner portions 28 extending inwardly from end portions 24 each at an angle thereto. The inner portions 28 are disposed along a common axis which is relatively parallel to the axis of the top portions 12 of frame 10.

The member 22 is formed to include a plurality of loops or hook like formations between the inner portions 28 and joining the same. In particular, the loops are formed to include a plurality of upward and outwardly extending portions 30, in the present illustration three such portions are shown, a plurality of central leg portions 32 each disposed generally vertically when the appliance is in a position of use, and a plurality of outwardly and downwardly extending portions 34, in the present illustration two such portions are shown. As shown in FIGS. 1 and 4, the inner portions 28 meet the legs 32 which, in turn, extend upwardly to corresponding loops 30, which, in turn, are joined by additional central leg portions 32 to the lower loops 34.

The face crib further comprises a forehead rest element generally designed 36 and carried by frame 10 on the top portion 12 thereof. The forehead rest 36 includes a relatively rigid supporting member 38 which is relatively thin, generally rectangular and curved in a lengthwise direction. The support member 38 is preferably of metal such as stainless steel or suitable lightweight alloys. As shown in FIG. 3, forehead rest 36 includes a pad element 40 of foam material secured by suitable hypoallergenic adhesive or the like (not shown) to the surface of member 38 which faces the head of the patient. The pad 40 preferably is several times greater in thickness and of the same general outline and perimeter as member 38. Further, pad 40 is provided with an exterior layer or coating 42 of mole skin material or the like which layer contacts the forehead region of the patient when the appliance is worn in a position of use. The lengthwise curvature of forehead rest 36 is of a degree such that it conforms to the curvature of the patient's forehead. The forehead rest 36 including foam pad 40 and mole skin 42 contacts the patient's forehead in the manner supporting and positioning the appliance and preventing slippage and undesired movement thereof in a manner which is uncomfortable to the patient. The forehead rest 36 is connected to the central portion of frame 10 at top portion 12 in a suitable manner, such as by a thin metal strip formed to have a portion midway of the ends which wraps tightly but movably around top frame portion 12 with the ends extending therefrom through a slit formed in member 38 (not shown) and then oppositely along the back surface of member 38 which is covered by pad 40. The connection of the forehead rest 36 to top frame portion 12 permits pivoting of the rest relative to the frame thereby enhancing the comfortable fit of the face crib.

The face crib of the present invention further comprises a pair of cheekbone pad elements generally designated 46 and carried by frame 10 at the lower side frame portion 16 thereof. The cheekbone elements 46 include a relatively rigid supporting member 48 generally rectangular in shape with one end being somewhat semicircular, and preferably of metal such as stainless steel or suitable light weight alloys. As shown in FIG. 4, the cheekbone elements 46 include a pad element 50 of foam material secured by suitable adhesive or the like (not shown) to the inner surface of member 48 which faces the cheekbone region of the patient's head when the frame is in a position of use. The pad 50 covers the entire interior surface and is of slightly greater thickness of member 48 than member 48. The cheekbone elements 46 can be provided with an optional exterior layer (not shown) or coating of mole skin material or the like which layer covers the foam material 50 and contacts the cheekbone region of the patient's head when the appliance is worn in a position of use. The cheekbone elements 46 engage the patient's cheekbone region in a manner supporting and positioning the face crib thereupon and preventing slippage or undesired movement thereby enhancing stability of the appliance all in a manner which is comfortable to the patient. The cheekbone elements 46 illustrated in the present embodiment are soldered to lower side frame portions 16 as shown at 52. Alternatively, the cheekbone elements 46 could be anchored by frame 10 by other suitable means.

The face crib in accordance with the present invention is utilized in the following manner. The appliance is worn on the patient's head adjacent the face with forehead rest 36 and cheekbone pad elements 46 contacting the forehead and cheekbone regions, respectively, of the patient. The frame 10 is adjacent the patient's head generally outlining or circumscribing the region of the face lateral to the eyes, nose and mouth. Specifically, the forehead rest 36 contacts the patient's forehead in conformity with the curvature thereof. The top frame portion 12 is closely adjacent the patient's forehead region, the upper side frame portions 14 are located closely adjacent the patient's head above the cheeks between the eyes and the ears, and the lower side frame portions 16 are located closely adjacent the patient's cheeks and jaw. Bottom frame portion 18 connects mouth bow 20 such that the mouth bow is adjacent the patient's mouth when the appliance is in a position of use.

Force applying means, preferably elastic rubberband like elements, are connected at one end to the member 22 of mouth bow 20 and at the other end thereof to particular teeth of the patient's in a manner applying a pulling force to the teeth in a direction toward the member 22. Referring to FIG. 5, the upper and lower molar teeth of the patient are designated 64 and 66, respectively, and an oral anchor 68 is attached to a rear lower molar. One elastic element 70 is joined to anchor 68 and to the leg and hook formations 32 and 34, respectively of the member 22 in a manner such that the band 70 is in tension. As a result, a drawing or pulling force is applied to the region of the rear lower molar having anchor 68 in a direction toward member 22 in the front of the patient's mouth. Simultaneously, a force of substantially equal magnitude to that of the pulling force is applied reciprocally to the forehead rest and cheekbone pad element which holds the appliance in a relatively stationary position on the patient's head. Another elastic element (not shown) is joined to the leg and hook formations 32,34, respectively, of member 22 and to the corresponding tooth on the opposite side of the patient's mouth. Similar forces are applied to the region of the tooth in the direction of member 22 as described above in connection with the other side of the patient's mouth.

The foregoing illustrates an orthodontic function which allows forward pulling on the mandibular arch. The foregoing is not limiting but shown for the purposes of illustration only. Consequently, the appliance in accordance with the present invention can function to bring an individual tooth forward to close the space between adjacent teeth and also bring the maxillary or mandibular arch forward as a result of the drawing or pulling force applied thereto.

When installing the appliance on the patient as in the foregoing examples, the elastic element 70, shown in FIG. 5, is first joined to the appropriated teeth and then simply looped over particular ones of hook formations 30 or 34 of member 22. Typically, an elastic element connected to lower teeth will be fitted at opposite ends over the upwardly extending hook formations 30, while those joined to the upper teeth will be looped over the downwardly extending hook formations 34. While the foregoing illustration includes the use of oral anchors, in some instances the rubberband element simply can be looped at one end around a selected tooth and at the other end around the hook formation. In all instances the teeth to which the forward pull is applied will be located rearwardly of the regions where the forehead rest and cheekbone pad elements contacts the patient so that the tension force exerted on the respective elements will hold the appliance in a relatively stationary position on the patient's head.

Frame 10 is of relatively light weight metal such as stainless steel and is of a cross sectional dimension which is sufficiently small so that the frame is bendable or otherwise formable to permit its adjustment to the shape of the patient's head and face. In particular, adjustment of the frame portion 10 can be made by using pliers of the like at the junctions of frame portions 12 and 14, 14 and 16, 16 and 18 and/or 18 and 24. Such adjustments enable the frame portion 10 to conform closely to the contour of the forehead. This is particularly important to insure that the appliance stays in place while the patient is sleeping. By adjusting the junctions of the frame portions, the location of the forehead rest element 36 can be raised or lowered relative to the patient's forehead region thereby accommodating long and short faces. In addition, forehead rest element 36 should be adjusted to be positioned above the eyebrows for maximum surface contact allowing the patient to take and have freedom of lower jaw movement without displacing the appliance. The mouth bow 20 can be adjusted about points 18 and 24 and should be positioned such that portions 24 and 28 of mouth bow 20 are aligned with the patient's teeth which is usually the most favorable placement to facilitate protraction of the lower arch. If the elastic pull is below the mouthline the incisors intrude and flare as they advance. If the elastic pull is above the mouthline, the molars extrude with occlusal plane (bite level) change.

It will be understood that the forehead rest and cheekbone rest elements are for purposes of illustration only and not limitation. Therefore, an appliance including a varying number of forehead rests and/or a varying number and size cheekbone rest elements is within the scope of the present invention.

The face crib is held in place by the counter force of the elastic tension means exerted on the cranial portions of the patient's head by the forehead rest and pair of cheekbone rest elements. Further, the face crib in accordance with the present invention could include a strap means, generally designated 56, and adapted to be connected to frame 10 and wrap around the back of the patient's head to further support the face crib therein as illustrated in FIGS. 1 and 2. The upper side frame portion 14 includes two hook members 54 projecting rearwardly therefrom. The strap means 56 is comprised of a band 58 and means 60 including a pair of hooks 62 which cooperatively retain a strap 64 thereupon from hook members 54 of frame portion 14 thereby retaining the strap in a taut position on the back of the head. Any means adapted to connect to frame 10 and retain a strap taut around the patient's head is within the scope of the present invention.

The appliance typically is worn for a prescribed length of time each day, often while the patient is reading, watching television or engaging in similar activities requiring use of the eyes. The shape and dimensions of the frame 10 provide a large open space or region in the area of the patient's eyes so as not to interfere with vision. Furthermore, this together with the adjustment points on the frame allows the patient to wear glasses simultaneously with the appliance. The forehead rest element and cheekbone rest elements have liners or air breathing hypoallergenic foam material covered with mole skin. The soft air breathing material prevents skin irritation while at the same time preventing slippage of the appliance when supported on the cranial portions of the patient's head thereby enhancing stability. Accordingly, this new and improved face crib accomplishes several treatments goals while not having unfavorable effects upon the temporo mandibular joint components, condylar positioning, nor the hyoid and mandibular complex.

It will be undersold that the foregoing description and illustration is by way of example only and that such modifications and changes as may suggest themselves to those skilled in the art are intended to fall within the scope of the present invention as defined by the appended claims.

I claim:

1. An orthodontic appliance comprising:
   a frame for wearing on the head of the patient and shaped to outline the area of the patient's face including the forehead, eyes, nose and mouth;
   tension force applying means having two ends, said tension applying means adapted to be connected at one end to said frame forwardly of the mouth and adapted to be operatively connected at the other end thereof to selected teeth of the patient, said tension applying means exerting an outward tension force for pulling the selected teeth in a direction toward said frame; and
   means carried by said frame for contacting exclusively the forward cranial so that pressure is not exerted against the lower jaw and subsequently transmitted unfavorably against the mandibular joint as it relates to the temporal bone and associated disc, said means cooperating with said tension applying means such that said means simultaneously pushes against the cranial region of the head when said tension applying means pulls the selected teeth in a direction toward said frame, thereby supporting said frame in a relatively stationary position entirely against the cranial region of the patient's head.

2. An apparatus according to claim 1 wherein said tension force applying means is elastic.

3. An apparatus according to claim 1, wherein said means carried by said frame is a forehead rest element.

4. An apparatus according to claim 1, wherein said means carried by said frame includes a forehead rest element and two spaced apart cheekbone pad elements and adapted to contact the forward cranial portions of the patient's head.

5. Apparatus according to claim 1, wherein said frame is continuous and of metal having a cross sectional dimension sufficiently small that said frame is relatively light in weight and is bendable or otherwise formable to permit adjustment to the shape of the patient's head and face.

6. Apparatus according to claim 1, wherein said frame is held stationary by bands attached thereto and adapted to extend around the patient's head facilitating securement of the frame to the head.

7. Apparatus according to claim 1, wherein said appliance is a face crib.

8. An orthodontic appliance comprising:
   a frame for wearing on the head of the patient and shaped to outline the area of the patient's face including the forehead, eyes, nose and mouth, said frame including a top portion closely adjacent and conforming to the shape of the patient's forehead, a pair of parallel spaced apart upper side portions extending from opposite ends of said top portion and located closely adjacent and conforming to the opposite sides of the patient's face including the cheekbone regions, a pair of parallel spaced apart lower side portions extending inwardly from said upper side portions and conforming to the opposite sides of the patient's face including the cheekbone regions and upper and lower jaw regions, and a bottom portion extending from said lower side portion and closely adjacent the patient's mouth;
   tension force applying means having two ends, said tension applying means adapted to be connected at one end to said frame forwardly of the mouth and adapted to be operatively connected at the other end thereof to selected teeth of the patient, said tension applying means pulling the selected teeth in a direction toward said frame; and
   means carried by said frame for contacting exclusively the forward cranial region of the patient's head so that pressure is not exerted against the lower jaw and subsequently transmitted unfavorably against the mandibular joint as it relates to the temporal bone and associated disc, said means being associated with said tension means such that said means simultaneously pushes against the cranial region of the head when said tension means pulls the selected teeth in a direction toward said frame, thereby supporting said frame in a relatively stationary position entirely against the cranial region of the patient's head.

9. An apparatus according to claim 8, wherein said bottom portion of said frame further include a member fixed thereto and extending therefrom in a manner to be forwardly of the patient's mouth when said appliance is in a position of use.

10. Apparatus according to claim 9, wherein said member includes a plurality of hook formations forwardly of the patient's mouth, said tension applying means being connected to said hook formations at one end thereof.

11. Apparatus according to claim 10, wherein said hook formations include a plurality of upwardly projecting hook formations and a plurality of downwardly projecting hook formations.

12. An orthodontic appliance comprising:
a frame for wearing on the head of the patient and shaped to outline the area of the patient's face including the forehead, eyes, nose and mouth;
tension force applying means having two ends, said tension applying means adapted to be connected at one end to said frame forwardly of the mouth and adapted to be operatively connected at the other end thereof to selected teeth of the patient, said tension applying means pulling the selected teeth in a direction toward said frame; and
a forehead rest element pivotally connected to said frame in conformity with the curvature of the patients forehead for contacting exclusively the forward cranial region of the patient's head so that pressure is not exerted against the lower jaw and subsequently transmitted unfavorably against the mandibular joint as it relates to the temporal bone and associated disc, said forehead rest element being associated with said tension means such that said forward rest element simultaneously pushes against the cranial region of the head when said tension means pulls the selected teeth in a direction toward said frame, thereby supporting said frame in a relatively stationary position entirely against the cranial region of the patient's head.

13. Apparatus according to claim 12, wherein said forehead rest element includes a rigid backing member and air breathing anti-friction material fixed to said backing member for contacting the forehead of the patient.

14. An orthodontic appliance comprising:
a frame for wearing on the head of the patient and shaped to outline the area of the patient's face including the forehead, eyes, nose and mouth;
tension force applying means having two ends, said tension applying means adapted to be connected at one end to said frame forwardly of the mouth and adapted to be operatively connected at the other end thereof to selected teeth of the patient, said tension applying means pulling the selected teeth in a direction toward said frame; and
two spaced apart cheekbone pad elements carried by said frame for contacting exclusively the forward cranial region of the patient's head so that pressure is not exerted against the lower jaw and subsequently transmitted unfavorably against the mandibular joint as it relates to the temporal bone and associated disc, said cheekbone pad elements simultaneously push against the cranial regions of the head when said tension means pulls the selected teeth in a direction toward said frame, thereby supporting said frame in a relatively stationary position entirely against the forward cranial region of the patient's head.

15. Apparatus according to claim 14, wherein said cheekbone pad elements are fixed to said frame at opposite sides thereof.

16. Apparatus according to claim 14, wherein said cheekbone pad elements are substantially planar, formed of rigid material and have air breathing anti-friction material on the inner surface thereof for contacting the cheekbone region of the patient's head.

17. An apparatus according to claim 14, wherein said cheekbone elements are adapted to contact the cranial portion of the patient's head below the eyes.

18. An orthodontic mid-facial orthopedic appliance comprising:
a frame for wearing on the head of a patient and shaped to outline the area of the patient's face including the forehead, eyes, nose and mouth;
a forehead rest element carried by said frame for contacting exclusively the patient's forehead for supporting the frame thereagainst;
two spaced pad elements carried by said frame for contacting exclusive the cheekbone area of the patient's head for supporting the frame thereagainst;
a member fixed to said frame and extending therefrom in a manner to be forwardly of the patient's mouth when said appliance is in a position of use, the region between said member portion and said forehead rest within said frame being open so as to allow unobstructed vision for the patient; and
tension force applying means having two ends, said tension applying means adapted to be connected at the other end thereof to selected teeth of the patient, said tension applying means exerting an outward force for pulling said selected teeth in a direction toward said member portion and simultaneously holding said appliance in place on the patient's head such that said frame is supported entirely by the cranial portions of the patient's head so that pressure is not exerted against the lower jaw and subsequently transmitted unfavorably against the mandibular joint as it relates to the temporal bone and associated disc.

19. A method of straightening teeth and the associated arch using an orthodontic appliance comprising:
providing a stationary supporting by contacting exclusively the cranial portions of the patient's head so that pressure is not exerted against the lower jaw and subsequently transmitted unfavorably against the mandibular joint as it relates to the temporal bone and associated disc; and
applying an outward tension force between the stationary support and teeth to move and position the teeth and associated arch forward and simultaneously hold the stationary support exclusively against the cranial portion of the head.

20. The method according to claim 19, wherein said stationary support comprises a frame adapted to be worn on the head of the patient and shaped to outline the area of the patient's face including the eyes, nose and mouth.

21. The method according to claim 20, wherein said frame includes a forehead rest element carried thereon and adapted to contact the patient's forehead area.

22. The method according to claim 20, wherein said frame includes a pair of cheekbone pad elements spaced on either side of said frame and adapted to contact the patient's cheekbone area.

23. The method according to claim 20, wherein said frame includes a forehead rest element and a pair of cheekbone pad elements adapted to contact the cranial portion of the patient's head.

24. The method according to claim 19, wherein said tension force is elastic.

25. The method according to claim 24, wherein said elastic is adapted to be connected at one end to said frame forwardly of the mouth and at the other end thereof to selected teeth of the patient.

26. The method according to claim 19, wherein said cranial portion of the head include the forehead and cheekbone regions.

27. The method according to claim 19, wherein said orthodontic appliance is a face crib.

* * * * *